United States Patent
Frey et al.

(10) Patent No.: US 9,844,343 B2
(45) Date of Patent: Dec. 19, 2017

(54) BIOSENSOR AND METHOD FOR PROVIDING A BIOSENSOR

(71) Applicant: Roche Diagnostics Operations, Inc., Indianapolis, IN (US)

(72) Inventors: Stephan-Michael Frey, Griesheim (DE); Oliver Kube, Worms (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 503 days.

(21) Appl. No.: 13/930,785

(22) Filed: Jun. 28, 2013

(65) Prior Publication Data

US 2013/0296664 A1 Nov. 7, 2013
US 2017/0311892 A9 Nov. 2, 2017

Related U.S. Application Data

(63) Continuation of application No. PCT/EP2011/072732, filed on Dec. 14, 2011.

(30) Foreign Application Priority Data

Dec. 30, 2010 (EP) .................................. 10197413

(51) Int. Cl.
*A61B 5/00* (2006.01)
*A61B 5/145* (2006.01)
(Continued)

(52) U.S. Cl.
CPC ........ *A61B 5/6846* (2013.01); *A61B 5/14532* (2013.01); *A61B 5/14865* (2013.01);
(Continued)

(58) Field of Classification Search
CPC ............ A61B 5/14532; A61B 5/14865; A61B 2562/12
See application file for complete search history.

(56) References Cited

U.S. PATENT DOCUMENTS 5,792,943 A * 8/1998 Craig .................. B32B 38/06
210/198.2
6,103,033 C1 10/2012 Say et al.
(Continued)

FOREIGN PATENT DOCUMENTS

EP 1870127 A1 12/2007
EP 1909098 A1 4/2008
(Continued)

OTHER PUBLICATIONS

Guiseppi-Elie et al (Design of a Subcutaneous Implantable Biochip for Monitoring of Glucose and Lactate, 2005, IEEE Sensors Journal, 5(3): 345-355).*

*Primary Examiner* — Jacqueline Cheng
*Assistant Examiner* — Angeline Premraj
(74) *Attorney, Agent, or Firm* — Bose McKinney & Evans LLP

(57) ABSTRACT

A biosensor is proposed for insertion into the subcutaneous tissue of a user wherein the biosensor includes at least one flexible substrate (2) and at least one electrode (5) on at least one surface (9) of the substrate and at least one contacting element (3). The contacting element is connected to the electrode. The substrate has at least one kink (4), at which the substrate is at least partly kinked such that the surface is subdivided into at least two interconnected outer surfaces (9a, 9b, 9c).

13 Claims, 5 Drawing Sheets

(51) Int. Cl.
 *A61B 5/1486* (2006.01)
 *A61N 1/05* (2006.01)

(52) U.S. Cl.
 CPC ......... *A61B 2562/12* (2013.01); *A61N 1/0504* (2013.01); *Y10T 29/49155* (2015.01)

(56) References Cited

U.S. PATENT DOCUMENTS

| | | | |
|---|---|---|---|
| 2003/0143113 A2* | 7/2003 | Yuzhakov | A61B 5/1411 422/420 |
| 2004/0043477 A1* | 3/2004 | Schibli | G01N 27/3272 435/287.1 |
| 2005/0196747 A1* | 9/2005 | Stiene | B01L 3/502792 435/4 |
| 2006/0024774 A1 | 2/2006 | Zocchi | |
| 2006/0030789 A1* | 2/2006 | Allen | A61B 5/1411 600/583 |
| 2008/0129280 A1 | 6/2008 | Kaimori et al. | |
| 2008/0135408 A1 | 6/2008 | Sjolander | |
| 2009/0093695 A1* | 4/2009 | Nakamura | A61B 5/157 600/347 |
| 2010/0025239 A1 | 2/2010 | Cho | |

FOREIGN PATENT DOCUMENTS

| | | |
|---|---|---|
| EP | 2163190 A1 | 3/2010 |
| WO | 2006116765 A2 | 11/2006 |
| WO | 2010014959 A2 | 2/2010 |
| WO | 2010114998 A1 | 10/2010 |

* cited by examiner

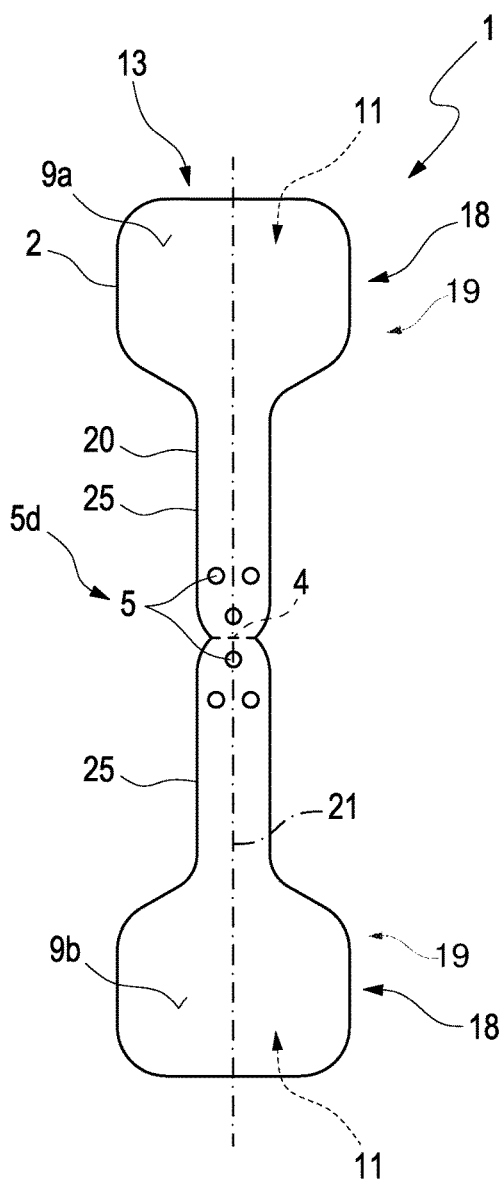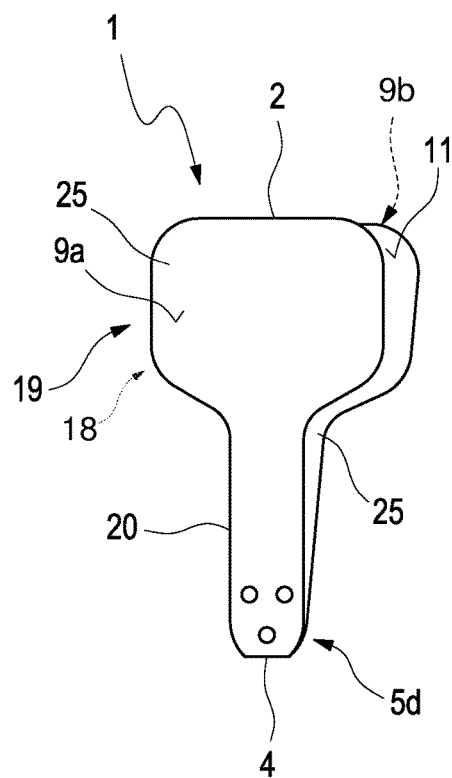
Fig. 6 a
Fig. 6 b

BIOSENSOR AND METHOD FOR PROVIDING A BIOSENSOR

CROSS-REFERENCES TO RELATED APPLICATION(S)

This application is a continuation of and claims priority to International Patent Application no. PCT/EP2011/072732 which was filed on Dec. 14, 2011 which in turn claims priority to European patent application no. 10197413.7 filed on Dec. 30, 2010.

FIELD OF THE INVENTION

The invention lies in the field of biosensors, specifically biosensors for continuously measuring bodily fluid parameters in the body of a user. The invention relates to a biosensor for insertion into subcutaneous tissue of the user. The invention furthermore relates to a substrate blank for producing a biosensor and an insertion kit for inserting a biosensor into subcutaneous tissue of a user as well as to a method for producing a biosensor.

DESCRIPTION OF THE RELATED ART

In addition to so-called point measurements, which are merely carried out once or a few times, the prior art has also disclosed, inter alia, long-term monitoring of one or more physiological parameters. In the following text, the invention will be substantially described with reference to physiological parameters in the form of analyte concentrations of one or more analytes in a bodily fluid of the user, for example a human or animal patient, independently of whether an illness is in fact present or whether there should merely be monitoring of healthy users. Without restricting further possible applications, the invention will be described in the following text with reference to blood-glucose monitoring. However, in principle, the invention can also be implemented with other types of analytes and/or implemented to monitor other types of physiological parameters.

In recent times, continuous glucose measurements in the interstitial fluid of the user, which is also referred to as continuous monitoring (CM), is becoming more and more established. This method is suitable for managing, monitoring and controlling a diabetes state for example. Here, the prior art has in the meantime disclosed directly implanted electrochemical sensors which are often also referred to as needle type sensors (NTS). Here, the active sensor region is brought directly to a measurement point, which is generally arranged in the interstitial tissue and which converts glucose into electric charge, for example by using an enzyme (for example glucose oxidase, GOD or glucose dehydrogenase), which charge is correlated to the glucose concentration and can be used as measurement variable. Examples of such transcutaneous measurement systems are described in U.S. Pat. No. 6,360,888 B1 or in US 2008/0242962 A1. Continuous monitoring systems generally capture measured values, e.g. glucose measured values, at regular or irregular intervals. By way of example, glucose measured values can be captured at an interval of 5 minutes or less in the case of implanted sensors.

The prior art has disclosed various sensors for measuring bodily fluid parameters in the body of a user, which sensors are able to convert various molecules continuously on the basis of electrochemical biosensors and are able to determine measurement results for these parameters. Thus, for example, U.S. Pat. No. 6,103,033 has disclosed an electrochemical biosensor which can be introduced into the patient for continuous measurement of glucose. On a planar surface of a flexible substrate, this biosensor has a plurality of electrodes which are connected to contacting elements by means of conductor tracks. This renders it possible to measure a parameter converted at the electrodes, which parameter generates electrical signals at the electrodes. As a result of the contacting elements being contacted by a measuring instrument, these electrical signals are converted into a parameter value, which is made available to the user.

US 2008/0135408 also discusses a biosensor with a simple arrangement of working electrode, counter electrode and reference electrode on a planar substrate, wherein in turn the electrodes are connected to contacting elements, which in turn are able to be connected to a measuring instrument. Moreover, there are biosensors which have not only one working electrode but which have available a working electrode, distributed over various positions on the surface of the sensor, and moreover are able to have a plurality of such working electrodes on the front and rear side of a biosensor.

WO 2010/014959 also describes options being able to apply a plurality of electrode pairs made of working and counter electrode onto a substrate surface.

Moreover, EP 1 870 127 A1, WO 2006/116765 A2, and WO 2010/114998 A1 describe multi-electrode arrays, which serve to be inserted into the body in order to stimulate tissue or provide therapy against pain.

Even though the prior art has already shown options of how to provide continuously measuring biosensors, which have to be inserted into the body of the patient, with various geometrically formed and applied electrodes as efficiently as possible, the prior art discloses no adapted options for producing biosensors with more than one electrode in an efficient and cost-effective manner. Since conventional printing methods for applying electrical components, such as, for example, printing methods such as for example screen printing, can in each case only be used to print one side of a surface of the substrate, the systems from the prior art with more than one printed surface have the disadvantage that this requires a number of process steps on both substrate surfaces to be repeated. This leads to a very complicated and cost-intensive production process for biosensors with more than one substrate surface, which sensors are provided with electrodes, contacting elements and conductor tracks. Moreover, the prior art only describes systems which only have one carrier on which the electrical components are applied. This restricts the option of applying more electrical components onto the substrate over a predetermined length of the part to be inserted of the NTS than is allowed by this predetermined length.

OBJECT OF THE INVENTION

It is therefore an object of the present invention to specify devices and methods, which, at least to a great extent, avoid the disadvantages of known devices and methods. In particular, a method for producing a biosensor should be specified which can render it possible, in a simple way, to apply a multiplicity of electrical components, such as, for example, contacting elements, conductor tracks and electrodes, onto a surface of a sensor substrate. In particular, a method should be specified which has a step rendering it possible to subdivide the surface on which the various elements are to be applied into a plurality of interconnected outer surfaces of the biosensor. This object is achieved by the invention with the features of the independent patent claims. Advantageous developments of the invention, which can be realized individually or in any combination, are illustrated in the dependent patent claims.

SUMMARY OF THE INVENTION

It is against the above background that the present invention provides certain unobvious advantages and advancements over the prior art. In particular, the inventors have recognized a need for improvements in biosensors and methods for producing biosensors.

In a first embodiment of the present invention, a biosensor is proposed for insertion into subcutaneous tissue of a user, wherein the biosensor comprises at least one flexible substrate and at least one electrode on at least one surface of the substrate and at least one contacting element, wherein the contacting element is connected to the electrode, wherein the substrate has at least one kink, at which the substrate is at least partly kinked such that the surface is subdivided into at least two interconnected outer surfaces.

As already mentioned above, the biosensor is designed to be inserted into subcutaneous tissue of a user, wherein, for example, use can be made of biocompatible materials, at least on an outer side of the biosensor which, in the inserted state, comes into contact with the body tissue.

The substrate, in particular prior to the kinking process, can have a planar design in particular. By way of example, the substrate can, after the kinking process, once again have a planar shape. However, alternatively, the substrate can also be available kinked in one or two further dimensions after the kinking process. As a result, the sensor can, during use, either have a substantially two-dimensional shape or even have a three-dimensional shape. Within the scope of the present invention, a planar substrate is understood to mean a substrate which has at least one substantially planar surface, preferably at least two substantially planar surfaces lying opposite to one another and preferably being substantially parallel. Here, the preferred planar design of the substrate should relate to the production process, wherein the actual biosensor during later use can also have a wholly or partly curved design, for example under the action of forces by the body tissue and/or under the action of forces by one or more mechanical devices, for example a body mount which holds the biosensor on a skin surface of the user and which, optionally, can bend a piece of the biosensor and/or of the substrate, for example for the purposes of contacting. However, in a rest state without the action of external forces, the substrate and/or the biosensor have a substantially planar design. Here, substantially planar is understood to mean a planar substrate, with, however, slight deviations from a planar design also being tolerable. By way of example, surface curvatures with a radius of curvature of more than 10 mm, preferably of more than 20 mm and in particular of more than 30 mm or more than 50 mm can be considered to be planar. Furthermore, the substantially planar surface can preferably have a flat design, with, however, slight roughness also been tolerable, for example a mean square roughness (rms) of less than 1 mm, more particularly of less than 0.5 mm. Substantially parallel is understood to mean completely parallel, with, however, deviations of no more than ±20°, in particular of no more than ±10° and particularly preferably of no more than ±5° also being tolerable within the scope of the aforementioned term. The preferably planar substrate particularly preferably has a thickness which is substantially less than the lateral extent of the preferably planar substrate, for example a thickness which is smaller by at least a factor of 10 than a length and/or a width of the planar substrate, preferably by at least a factor of 100. By way of example, the preferably planar substrate can have a thickness of no more than 4 mm, in particular a thickness of no more than 3 mm and particularly preferably of no more than 2 mm or even no more than 1 mm. The preferably planar substrate is therefore preferably a thin substrate with two substantially parallel and substantially planar surfaces lying opposite to one another.

Within the scope of the present invention, a flexible substrate is understood to mean a substrate which is deformed under conventional forces occurring during operation and more particularly in the inserted state, for example in the case of forces between 1 and 10 Newton, for example bending forces. The deformation can be reversible or else be irreversible. The deformation can be of plastic or else elastic nature. The deformation can be caused by a suitable choice of a substrate material and/or by a suitable choice of geometry of the substrate, for example by a thin, elongate substrate.

By way of example, the substrate can be produced from at least one substrate material. By way of example, this substrate material can be selected from a paper material, a polymer material, a ceramic material or a combination of the aforementioned and/or other materials. Use can also be made of multilayered substrate materials, for example laminates. The substrate of the biosensor can for example be provided with one or more functional elements, which can, for example, be applied to one or more surfaces. By way of example, this can, as will be explained in more detail below, be one or more electrodes and/or one or more contacting elements. Provision can also be made for other functional elements. These functional elements can be applied by means of one or more techniques which are known in principle, for example printing techniques and/or other techniques, in particular coating techniques, for example physical and/or chemical vapor deposition.

On at least one surface of its substrate, the biosensor respectively has at least one electrode and respectively has at least one contacting element, wherein the contacting element is connected to the electrode by e.g. a conductor track. In particular, the at least one electrode can comprise at least one working electrode and/or at least one reference electrode and/or at least one counter electrode. By way of example, the electrode can comprise at least one electrically conductive electrode surface. Furthermore, the electrode can comprise additional elements, for example at least one coating, for example an enzyme coating and/or at least one redox system. In principle, such electrodes are known from the prior art. However, in principle, other embodiments are also possible.

The biosensor preferably has at least one working electrode on at least one of the surfaces.

The substrate furthermore has the at least one kink, at which the substrate is kinked, at least in part. In principle, the kink can have any geometric shape. By way of example, the kink can comprise at least one kink line, along which the substrate is, for example, kinked in a linear fashion. However, more complex geometries are also possible. In principle, the kinking can occur with any radius; however, preferably with a radius of no more than 5 mm, in particular no more than 3 mm and particularly preferably of no more than 1 mm. By way of example, the outer surfaces can have a substantially planar design outside of the kink.

During the kinking process, at least one piece of the substrate is kinked with respect to the other piece of the substrate, and so the two pieces are no longer arranged flush with one another. As a result of this, the surface, on which for example all elements for carrying out measurements using the biosensor can be applied, is subdivided into at least two pieces. Since the two pieces of the substrate or the biosensor preferably move toward one another during this kinking process, at least two inner surfaces are preferably created, which inner surfaces move toward one another and point at one another during the kinking process. The surfaces on the same substrate piece respectively lying opposite to the two optional inner surfaces are referred to as outer surfaces of the substrate. These at least two outer surfaces point away from one another.

Within the scope of the present invention, kinking is understood to mean a process in which a surface of a body, for example of the substrate, is at least largely irreversibly deformed by the action of mechanical forces. In particular, a kink can be created during the kinking, at which kink a surface curvature of the substrate experiences a jump-like change. In this context, at least largely irreversible means that the substrate preferably does not independently return to its original shape prior to the kinking after the kinking process without the action of forces. The kink preferably brings about a stable permanent bending of the two kinked surfaces or outer surfaces. Kinking is an active, deliberate process, which, in terms of its dimensions and direction, can be selected in a targeted fashion. As a result of the kinking process, the two kinked outer surfaces are preferably aligned at a particular angle with respect to one another. The angle can be selected freely, as will be explained in more detail below. The resultant fixation of the outer surfaces can for example be brought about by virtue of the fact that the substrate, at least in part, consists of a non-elastic material. Alternatively, or in addition thereto, the two kinked pieces can, at least at the kink, be fixed with respect to one another after the kinking. By way of example, the fixation can be an adhesive bonding or fastening of the two kinked pieces, preferably at the inner surfaces. It is preferable for the substrate not to be bendable any further, at least at the kink, in the kinking direction or against the kinking direction after the kinking process. Apart from that, the substrate can have an elastic and bendable design such that the remaining biosensor can during use adapt itself to the body into which it is inserted, without the biosensor losing its kinked basic structure. The result of this is that, after the action of external forces which bend a piece of the substrate of the biosensor, the biosensor preferably assumes its original shape again after the kinking process. The kink can constitute a discontinuity within the substrate, because the substrate preferably undertakes an abrupt directional change in its surface at this point. This is in contrast to the continuous directional change during a bending process, for example of the remaining substrate, for example during insertion and use. Consequently, after the kinking process of the surface, the kinked biosensor is also referred to as folded biosensor in the following text.

Furthermore, at least one electrically conductive component is preferably also kinked and/or folded during the kinking. By way of example, the electrically conductive component can be at least one piece selected from the group consisting of a contacting element, an electrode, a conductor track and further functional elements or at least two thereof. Structure and design of these electrically conductive components will still be explained in more detail later.

What can be achieved by kinking the substrate of the biosensor is that more than only one surface of the biosensor to be inserted can be equipped with electrodes and contacting elements, without, in the process, equipping more than one surface with active elements prior to kinking the biosensor substrate. By way of example, there can be at least one single-sided coating of the substrate prior to the kinking process, wherein, nevertheless, a biosensor coated on two sides can be created after the kinking process. However, it is furthermore feasible also to equip the inner sides of the biosensor with electrical components, such as electrodes and contacting elements.

During the kinking process, the biosensor is preferably kinked by an angle of substantially 180°, i.e., for example, by an angle of 180°±30°, preferably 180°±20°, in particular 180°±10° or even 180°±5°. The result of this is that the two inner faces can, for example, come to rest on one another or close to one another.

It follows that the invention can be designed in such a fashion that the biosensor or the substrate thereof is designed in such a manner, for example extended in such a way, that at least two sensor tongues are created, for example sensor tongues in the form of the outer surfaces which are preferably respectively only coated, for example printed, on one side. As a result of this, it is possible, for example, on the biosensor to hold twice as many electrode pairs, for example consisting of working electrode and counter electrode, on the same area of the biosensor than is the case in conventional biosensors. After the coating, the biosensor can be folded or kinked and can subsequently be adhesively bonded to a connector which can ensure contacting with a measuring unit.

The substrate can more particularly have a planar embodiment, in particular prior to the kinking process. After the kinking process, the substrate can, for example, once again have a planar shape, as described above by the kinking by 180°. Alternatively, the substrate can also for example have a non-planar design after the kinking process, in particular after a first kinking process. By way of example, this can occur as a result of one or more kinking processes with a kink angle which deviates from 180°. By way of example, the substrate can be available in a kinked fashion in one or two further directions after the kinking process. Thus, during use, the sensor can either have a substantially two-dimensional shape or even have a three-dimensional shape. By way of example, a three-dimensional shape can be achieved by virtue of the fact that the substrate has more than one kink about which the substrate is kinked to form the sensor which is ready for use. These further kink or kinks can be on or in the substrate, parallel to the first kink or at a tilted angle. By way of example, this angle between the first and the further kinks can lie between 1° and 90°, for example depending on the intended three-dimensional structure of the sensor. By way of example, the substrate can experience a first kinking process at the first kink and experience a second kinking process at a second kink, which is at a distance from the first kink. Alternatively, it is also possible for the substrate to be kinked transversely with respect to the first kinking process in the second kinking process. Here, the first kink can also itself be kinked or the second kink is situated in a different region.

Further kinking processes can be carried out in parallel, obliquely or transversely with respect to one of the first two kinking processes, and so a sensor with a multiply folded three-dimensional structure is created.

A second kinking process is preferably carried out at a second kink, which is arranged parallel to the first kink. The two kinking processes can occur at the same time or be carried out in succession. In both kinking processes, the substrate is preferably respectively kinked by approximately 90° to 150°, particularly preferably by 110° to 130°. If the two kinking processes are undertaken in the same direction, a preferred embodiment has a biosensor with a triangular shape. The biosensor with two parallel kink lines has three outer surfaces after the kinking process, which outer surfaces can respectively be provided with functional elements, such as electrodes or contacting elements. By way of example, only one of the three outer surfaces may be provided with electrodes and contacting elements. Alternatively, it is possible for two or else three of the outer surfaces to be provided with electrodes and contacting elements. In an alternative embodiment, a contacting element is only applied to one of the three outer surfaces, which contacting element is connected to a plurality of working electrodes on two or three outer surfaces by means of conductor tracks. Additionally, one, two or each outer surface can have a counter electrode and/or a reference electrode.

Additionally, further parallel or oblique kinks can also be introduced in addition to the first or second kink. The two or all kinking processes can take place either successively or parallel in time with respect to one another.

One or more functional elements, such as working electrode, counter electrode, reference electrode or contacting element, may be situated on all outer surfaces created after the various kinking processes. Thus, for example, both a contacting element and a working electrode, connected by a conductor track, may be arranged on one outer surface. Furthermore, a counter electrode and/or a reference electrode, or a combination of counter and reference electrode, may be arranged on this outer surface. However, all further combinations of functional elements on the various outer surfaces and inner faces of the biosensor are also feasible. Thus, electrodes on one outer surface may be connected to at least one contacting element on another outer surface or an inner face of the biosensor by means of conductor tracks.

In particular, the biosensor can be designed in such a way that at least one electrode is arranged in each case on at least two of the outer surfaces.

At least one conductor track can preferably be arranged between the at least one contacting element and the at least one electrode. Provision can also be made for a plurality of conductor tracks, particularly if provision is made for a plurality of contacting elements and a plurality of electrodes.

In a preferred embodiment, the biosensor is embodied in such a way that the outer surfaces lie in at least two planes arranged substantially parallel to one another. In this context within the scope of the present invention, substantially means that the two outer surfaces are arranged with respect to one another in such a way that, except for in the region of the kink, the two outer surfaces extend parallel to one another. There may be a deviation of no more than 20°, preferably of no more than 10°, particularly preferably of no more than 5° from this 180° arrangement of the two outer surfaces, which should still be subsumed by the phrase arranged substantially parallel.

In particular, the biosensor can be designed in such a way that the substrate is subdivided into at least two interconnected substrate pieces by the kink, wherein the substrate pieces are connected, more particularly adhesively bonded, to one another at least in part. In order to enable fixation of the two substrate pieces to one another, and hence of the two outer surfaces as well, it is possible, in particular, to adhesively bond the two inner faces to one another. By way of example, adhesive bonding can be brought about by brief heating of the substrate in order to soften the substrate material and subsequent pressing together. Alternatively, use can be made of one or more adhesives in order to interconnect the inner faces.

After the kinking process, one or more elements, such as e.g. electrodes, contacting elements and conductor tracks, can be applied both to one and to both outer surfaces. If elements are attached to both outer surfaces, one or more elements on the one outer surface can also be connected to one or more elements on the other outer surface, for example by means of one or more connecting elements, which can extend over the kink. By way of example, these can be one or more conductor tracks. Thus, for example, it is conceivable that at least one electrode was applied to a first outer surface and at least one contacting element was applied to the second outer surface, which are connected by a conductor track which extends over the kink between the at least one electrode and the at least one contacting element.

As an alternative to a cohesive connection between the two substrate pieces, or in addition thereto, use can be made of one or more other connection techniques, for example force-fit and/or interlocking connections. Thus, one option of affixing the two substrate pieces of the biosensor against one another after the kinking consists of providing one or more webs between the outer surfaces. Thus, for example, it is possible to fix the two substrate pieces with respect to one another by further kinking of the substrate at one or both ends of the kinked biosensor. In addition or as an alternative thereto, webs can be attached to a piece of the substrate which are kinked about the kinked substrate after the first kinking process in order thus to fix the two kinked substrate pieces, for example in a force-fit and/or interlocking fashion.

At least one working electrode and at least one reference electrode and/or at least one counter electrode are preferably arranged in each case on the substrate of the biosensor.

At least one electrode is preferably arranged in each case on at least two of the outer surfaces. Preferably, at least two of the outer surfaces can respectively have at least one working electrode and respectively have, for both outer surfaces independently of one another, at least one electrode selected from the group consisting of a reference electrode and a counter electrode, for example a working electrode and a counter electrode or a working electrode and a reference electrode or a working electrode, a counter electrode and a reference electrode.

Additionally, at least one contacting element, i.e. an element which enables electrical contact to be established, can be arranged on at least one of the outer surfaces, preferably on each outer surface. It is preferable for in each case one electrode to be connected to at least one contacting element via at least one conductor track. At least one contacting element and/or at least one electrode is preferably arranged on both the first and the second outer surface.

In a further embodiment, at least two of the outer surfaces respectively have at least one working electrode and respectively have at least one reference electrode and/or counter electrode. In an alternative embodiment, it is also possible for a plurality of sets of working electrodes with reference electrodes and/or counter electrodes to be present. The electrodes are preferably in each case connected to a contacting element. The contacting element can be situated on respectively the same outer surface or else be situated on a different outer surface to the respective electrode.

All combinations of one or more electrodes on one or more outer surfaces in combination with one or more contacting elements on one or more outer surfaces are feasible in various embodiments. Thus, it is feasible that at least one electrode or one contacting element is situated on one outer surface only. Moreover, there are embodiments in which at least one electrode is arranged on one outer surface only, but respectively one contacting element is arranged on at least two outer surfaces. It is just as feasible for respectively at least one electrode to be arranged on a number of outer surfaces, but for at least one contacting element to be situated on one outer surface only. In a further embodiment, it is feasible that at least one electrode and at least one contacting element are present on each outer surface. In a further embodiment, at least one electrode and at least one contacting element are applied to one outer surface only. An advantage of this is that no conductor tracks are kinked during the kinking process. In particular, the at least one kinking process can be carried out in such a way that no contacting element and/or no conductor track and/or no electrode extends over the kink. However, other embodiments are also possible.

In a preferred embodiment, at least one contacting element and at least one electrode are exclusively arranged on at least one of the outer surfaces. Furthermore, at least one conductor track, which connects the at least one contacting element to the at least one electrode, can be situated on at least one of the outer surfaces. By way of example, the at least one contacting element can be arranged on the same outer surface as the at least one electrode. Additionally, at least one further electrode can be situated on at least one further outer surface. Alternatively, the at least one contacting element can be arranged on a different outer surface to the at least one electrode.

In one embodiment, in which the at least two inner faces are preferably not in contact with one another after the biosensor is kinked, it is also optionally possible for at least one electrode, at least one contacting element and/or at least one conductor track to be arranged on one and/or both inner faces. It is also possible for a plurality of elements, e.g. at least one electrode and at least one contacting element, to be attached on one or both inner faces. The at least one electrode and the at least one contacting element are preferably interconnected by means of a conductor track. Furthermore, the electrodes on the inner face of the substrate can also be connected to one or more contacting elements on one of the outer surfaces.

If there is only one electrode on an outer surface and/or inner face of the biosensor, then the former can be connected via a conductor track to a contacting element on the respective opposite inner or outer surface. All conceivable combinations of electrodes with contacting elements on the inner or outer surfaces or inner and outer surfaces are feasible.

Depending on the design of the electrodes, each electrode is preferably connected to a contacting element via at least one conductor track. However, it is also feasible that a plurality of electrodes, which can be situated on one outer surface or inner face or on a number of outer surfaces or inner faces, are connected to only one contacting element, which can extend over one or more outer surfaces or inner faces.

The electrodes on the bio sensor can be of different types and design. By way of example, this can be a working electrode, reference electrode or counter electrode on the substrate. The reference electrode can be embodied separately from the counter electrode; however, it can also be wholly or partly unified with the counter electrode. It is preferable for at least one working electrode and at least one reference electrode and/or at least one counter electrode or a combination of reference and counter electrode to be arranged on the substrate. The at least one working electrode and the at least one reference or counter electrode can be arranged both on one outer surface or on one inner face, or else on two different faces, i.e. on an outer surface and an inner face or two outer surfaces or two inner faces.

In an alternative arrangement, the biosensor respectively has at least one working electrode and respectively at least one reference electrode and/or counter electrode on at least two of the outer surfaces. Additionally, at least one working electrode and/or at least one reference electrode and/or at least one counter electrode can likewise be arranged on the inner faces, as well as all conceivable combinations of the at least one working electrode, reference electrode and counter electrode.

As an alternative or in addition thereto, at least one contacting element and/or at least one electrode can be arranged on both the first and the second outer surface of the biosensor. At least one conductor track preferably connects the contacting element and the at least one electrode.

The kink is arranged in the contacting element in a further preferred embodiment. Here, the contacting element can, for example, be subdivided into two portions by the kink, wherein, for example, a first portion is arranged on a first one of the outer surfaces and a second portion is arranged on a second outer surface. In particular, this can lead to the situation where at least one contacting element is arranged on all outer surfaces. The at least one working electrode on an outer surface is preferably connected to that piece of the contacting element which is situated on the same outer surface. It is furthermore preferable for respectively all working electrodes, all reference electrodes and/or all counter electrodes to be connected to respectively one contacting element. The contacting element can extend over one outer surface only or across a number of outer surfaces.

In a preferred embodiment, both the contacting element and the conductor track consist of the same material. This material should have good electrical conductivity; this property is exhibited by e.g. copper, gold, silver, platinum or palladium, or alloys thereof. Alternatively, the contacting element and also the conductor tracks can consist of different materials. Further electrically conductive materials can be electrically conductive polymers or materials with a high carbon proportion. In principle, all electrically conductive materials can be used for this purpose.

Depending on their function, the electrodes can consist of different materials. Thus, a working electrode can have one or more components which enable a conversion of the parameter to be measured. In the case of a biosensor, these can, in particular, be one or more enzymes and/or receptors. By way of example, for detecting glucose as a parameter in the bodily fluid, use can be made of a working electrode which, for example, has glucose oxidase (GOD) or glucose dehydrogenase (GDh). Alternatively, it is naturally also possible for further parameters such as lactate, cholesterol, HbA1C or other parameters from blood or interstitial fluid to be converted and measured in the working electrode.

The biosensor preferably has at least one biochemical component. Molecules or organisms which are capable of undergoing a reaction upon contact with a parameter to be measured and/or which are capable of interacting with a parameter to be measured are referred to as biochemical components. In one embodiment of the invention, the biochemical component undergoes a chemical reaction upon contact with the parameter to be measured. By way of example, a parameter is a molecule or molecule group found in the sample to be measured. The biochemical components can be selected from the group consisting of an enzyme, an enzyme with a coenzyme, a receptor, an organelle, a bacterium, a virus or at least two thereof. By way of example, a component which can be detected optically, inductively, magnetically or electrochemically is created in the reaction of the biochemical component. This detectable component either can be captured directly by a detection means or is converted into a detectable component in one or more reactions. The same material used for the working electrode is preferably used as counter electrode, wherein, preferably, a reactive component, such as the enzyme or the receptors in this case, is not applied to the conductor track provided for the counter electrode, but only the carrier material from the working electrode without the enzyme.

By way of example, an electrically conductive component, such as e.g. a carbon paste, can be used as carrier material for the biochemical component.

By way of example, as is well known from the prior art, the reference electrode can be produced from Ag/AgCl or comprise this system. However, use can also be made of other reference electrodes as known from the prior art.

The biosensor can have various geometric shapes, as long as it is suitable for being introduced into the body of a patient and for contacting a measuring instrument by means of the contacting elements. This is preferably a biosensor which is only partly introduced into the body of the user. This piece, which is introduced into the body of the patient, should preferably have the electrodes in order to bring the body tissue to be measured into contact with the enzyme or the molecule to be converted.

In order to ensure an introduction of the biosensor which is as pain-free as possible, the substrate preferably has an elongate structure. Here, an elongate structure should be understood to mean a geometry which has an longitudinal extent and a width, wherein a dimension in the width is less than a dimension along the longitudinal extent, for example by at least a factor of 2, more particularly by at least a factor of 3 or even by at least a factor of 5. In particular, the substrate preferably has the elongate form in the region in which it is inserted into the body.

In particular, the biosensor can be embodied in such a way that the at least one electrode and/or at least one electrode and the at least one contacting element and/or at least one contacting element are situated on mutually opposite ends of at least one of the outer surfaces. By way of example, one or more electrodes and/or one or more contacting elements can be situated on an end side, i.e. a narrower side, of at least one of the outer surfaces, and at least one electrode and/or at least one contacting element can likewise be situated on an opposite end side. The above-described kink, for example the at least one kink line, can more particularly be situated on at least one of the end sides.

At the location at which the at least one electrode is situated, this preferred piece of the biosensor with an elongate shape can more particularly be referred to as shaft or tongue, wherein the shaft or the tongue can comprise at least one electrode region or wherein at least one electrode region can adjoin the shaft. The region in which the at least one contacting element is situated, which can also be referred to as contacting region, can for example be embodied separately from the electrode region and can for example have a wider structure compared to the shaft with the electrode region. This is particularly preferred, since the contacting elements can have a slightly wider structure in order to be able to connect the biosensor to a measuring instrument in a simple and uncomplicated fashion.

As illustrated above, the biosensor has a substrate with an elongate structure in a preferred embodiment. The at least one electrode and the at least one contacting element can more particularly be situated at mutually opposite ends of at least one of the outer surfaces. Here, an arrangement at one end should be understood to mean an arrangement directly at the end or an arrangement at a distance of no more than 5 mm from the end, in particular of no more than 3 mm from the end. By way of example, it is possible to arrange the electrode in the electrode region and/or the contacting element at the opposite end at a slight distance from the respective end. However, it is particularly preferred, particularly in respect of the contacting element, if the latter is arranged directly at the end, for example on a kink line.

The arrangement of electrodes and contacting elements at opposite ends of the biosensor can contribute to the piece with the electrodes, to be inserted, being able to have a significantly narrower design than the piece with the at least one contacting element, which is for example not inserted. By way of example, one end of the biosensor can carry the at least one contacting element, and an opposite end can carry the at least one electrode. This geometry can influence the design of the biosensor prior to kinking, depending on what shape the kinked biosensor should have at the end or at what location the at least one kink and hence the connecting substrate material should be arranged.

In particular, the substrate can, as explained above, comprise at least one substrate material. The substrate material is preferably a flexible material which can have a very thin embodiment. The substrate material should preferably be used in the form of a film, since this ensures simple production from band to band, and can moreover ensure simple cutting or stamping of biosensor geometries. The substrate particularly preferably has a planar design such that it has two planar surfaces. However, all other shapes and materials of substrate are also conceivable. By way of example, use can be made of casting processes for producing specific geometries of the substrate, or of plates from which very different substrate shapes can be cut out, removed by laser or stamped.

For the simple production of large numbers of biosensors, a multiplicity of biosensor blanks can be stamped from the preferably planar substrate, wherein remaining webs interconnect the multiplicity of biosensors such that these can furthermore be subjected to one or more process steps such as, for example, printing with enzyme pastes before they are detached. However, the shaping of the biosensors from a film blank can also take place after applying various substances for creating the contacting elements and electrodes.

The substrate material preferably has at least one polymer or consists of at least one polymer, more particularly at least one polyimide. The polymer preferably has a high insulation resistance in order to avoid short circuits between the electrodes. It is particularly preferable for the polymer to be biocompatible since it is introduced into the body of a user. Alternatively, or in addition thereto, the biosensor can have a biocompatible coating, for example in the form of a biocompatible membrane. As a further alternative or in addition thereto, the sensor can have a membrane which constitutes a diffusion barrier for the analyte, more particularly glucose.

In order to avoid e.g. leakage currents between various electrodes, an insulation varnish can be applied over the substrate with the applied electrodes and contacting elements and with the optionally applied conductor tracks. Moreover, this insulation varnish can protect the functional elements, such as contacting elements, conductor tracks and electrodes, applied to the substrate, from mechanical stresses. What the insulation varnish can additionally bring about is that the functional elements, such as contacting elements, conductor tracks and electrodes, which are situated at the kink can be kinked, e.g. during the kinking process, without mechanical tensile or pressure stresses. In the process, the insulation varnish encloses the functional elements, such as contacting elements, conductor tracks and electrodes, between itself and the substrate. The insulation varnish preferably has a thickness, at least at the kink, which substantially corresponds to the thickness of the substrate at the kink. In this case, substantially corresponding to the thickness means that the thickness deviation between insulation varnish and substrate is no more than 20%, preferably no more than 10%.

According to a further aspect of the present invention, a method is proposed for producing a biosensor, more particularly a biosensor for insertion into subcutaneous tissue of a user. In particular, the biosensor can be a biosensor for qualitative and/or quantitative detection of at least one analyte in a bodily fluid. In particular, the biosensor can be a biosensor in accordance with one or more of the above-described embodiments.

The proposed method comprises the following steps, which can preferably, but not necessarily, be carried out in the illustrated sequence. A different sequence is also possible. Furthermore, provision can also be made for additional method steps which have not been specified. Furthermore, individual or a number of method steps can also be carried out at the same time, overlapping in time or repeatedly, either individually or a number of these together. The method comprises the following steps:

providing at least one flexible substrate, more particularly a planar flexible substrate, applying at least one contacting element and at least one electrode connected to the contacting element to at least one surface of the substrate, kinking the substrate at at least one kink such that the surface is subdivided into at least two interconnected outer surfaces.

In particular, the sensor can have an elongate structure. In particular, the kinking can take place in a manner selected from the following: kinking parallel to an axis of longitudinal extent of the biosensor; kinking at an angle to an axis of longitudinal extent of the biosensor, more particularly substantially perpendicular to the axis of longitudinal extent of the biosensor, for example with a deviation from the perpendicular of no more than 20°, in particular of no more than 10° and particularly preferably of no more than 5°.

In particular, production can be such that a plurality of biosensors is produced in use. By way of example, a plurality of biosensors can be interconnected by one or more webs, for example by using a corresponding substrate blank.

By way of example, the kinking can occur during a step where a plurality of biosensors which are interconnected by one or more webs are detached. To this end, the film can for example be routed over a metal edge, which exerts an impulse on the biosensor at the kink such that the substrate is kinked at the kink and at the same time detached from the remaining biosensors. The kinking can alternatively also take place after the detaching step.

A biocompatible material should preferably be used as substrate since at least a piece of the substrate comes into contact with the body of the user. The substrate is preferably planar and is, for example, provided in tape form but can, as already mentioned previously, also be provided in a plate form or in any other form and geometry. It is also conceivable that the substrate is available in the form of a round wire, on which the functional elements for the biosensor can then be applied. The substrate is preferably equipped from one side, such that the application of the at least one contacting element and of the at least one electrode can be carried out on at least one surface of the substrate. The substrate is preferably not rotated during the production process of the biosensor; at best it is advanced horizontally. However, it is also conceivable that the substrate is fixed and the application of the functional elements is brought about by means of a moveable application installation. The application of the contacting elements or conductor tracks can be brought about by sputtering processes or immersion processes or screen printing processes.

If electrical components are applied both to the external surfaces and to the inner faces, the production can also take place simultaneously on both sides on the surfaces of e.g. the tape-ware. Alternatively, the substrate can also first of all be treated from one side and subsequently from the other side.

Depending on the nature of the electrode material, the electrodes can be applied with very different methods. In principle, these methods are sufficiently well known from the prior art. By way of example, use can be made of lithographic methods, screen printing methods, other printing methods, pipetting, chemical vapor deposition, physical vapor deposition such as e.g. deposition and/or sputtering and/or combinations of the aforementioned and/or other methods.

The substrate is preferably kinked at at least one kink after the application of the various functional elements, such as contacting elements, conductor tracks and electrodes, such that the surface is subdivided into at least two interconnected outer surfaces. This kink can be selected at different positions in the substrate. This kink preferably comprises a region with less substrate material in order to simplify the kinking process and to be able to carry it out in a targeted fashion at a specific location. This kink with less substrate material can be produced either by a notch in the substrate, by cutting out substrate, etching away substrate or perforating the substrate or using any other material ablation methods.

Depending on which functional elements should be present on which surfaces after the kinking process and depending on how the biosensor should finally be inserted into the body, kinking can take place either parallel to an axis of longitudinal extent of the biosensor or across an axis of longitudinal extent of the biosensor if the latter has an elongate structure. Specific embodiments in this respect are explained in more detail in the description of the figures in particular.

Advantages of the biosensors with the kinked surface in particular lie in the option of providing more than one surface of the sensor to be inserted for the reaction with the bodily fluid, while at the same time having a much simplified production method. As already mentioned the simplification for producing a sensor with functional elements on more than one outer surface in particular lies in the possibility of being able to apply the functional elements on only one surface of the sensor prior to the kinking process. By way of example, this can be brought about by single-sided printing methods. As a result of the subsequent kinking of the substrate of the sensor, the active region of the biosensor available for the measurement, in which, for example, the electrodes are situated, can be increased a number of times compared to single-strand biosensors. The number of electrodes available for the measurement can be at least doubled in this manner. This is particularly advantageous since the path in the subcutaneous tissue (subcutis) of the user can only be used in a small region of less than 10 mm for measuring the bodily fluid so as not to damage any other tissue. As a result, biosensors with greater precision can be achieved, since the accuracy and the reproducibility of a biosensor increases with each additional electrode. As a result of doubling the electrodes on the sensor surfaces, an increase in the comfort of wear for the user can be achieved if the biosensor is inserted at a preferred angle of 45° with respect the skin. This is particularly advantageous compared to a conventional, longer biosensor, which has to be inserted at a flatter angle, and hence with more risk, in order to introduce the same number of electrodes into the skin.

What can moreover be achieved by kinking the bio sensor is that initially materials only have to be applied onto one surface of the substrate of the biosensor, leading to a simplified production process and hence to a significant reduction in costs. What this can achieve in a simple fashion is that a large piece of the substrate surface is used for measuring the bodily fluid when the biosensor is inserted. Moreover, there is great variability in undertaking the contacting of the inserted biosensor since the kinking at very different locations, inter alia in the contacting element region, makes contacting possible on very different areas of the biosensor. This renders it possible to enable very different geometries of functional elements on different outer surfaces of the biosensor using conventional production methods on only one surface. This ensures an adaptation to very different geometries of measuring instruments, insertion systems and requirements of the user.

In a further aspect of the present invention, a substrate blank is proposed for producing a biosensor. This substrate blank should be able to be used for producing a biosensor in accordance with one or more of the above-described embodiments. The substrate blank has at least one electrode on at least one surface of the substrate and at least one contacting element, wherein the contacting element is connected to the electrode. The substrate has at least one kink, at which the substrate can at least in part be kinked such that the surface is subdivided into at least two interconnected outer surfaces.

In addition to the already mentioned functional elements such as the at least one contacting element and the at least one electrode and, optionally, at least one conductor track, the substrate blank thus has, as already mentioned above, at least one kink. In particular, this kink can for example comprise at least one kink line. In particular, the kink can comprise at least one weakening of a substrate material of the substrate, for example a local thinning of the substrate material. By way of example, the kink can be formed in a manner selected from: a slit, a perforation, a kink line with a groove or a combination therefrom.

This kink can be arranged symmetrically over the substrate blank, for example on mutually opposite locations on mutually opposite surfaces of the substrate blank; however, alternatively, it can also be introduced onto only one side of the substrate. The kink can be arranged symmetrically over the profile of the substrate such that the substrate is subdivided into two equal pieces after kinking, or else it can be arranged asymmetrically, such that one piece of the substrate is smaller than the other one after kinking. As a result, it is possible to obtain outer surfaces with different sizes or else with the same size. Furthermore, there can be more than one kink on the substrate such that the biosensor can be kinked at more than one location or can be kinked a number of times at one location.

In a preferred embodiment, a number of the material reduction measures can be used in a substrate blank in order to provide the kink. Thus, for example, there can be a notch on either one or both sides of the substrate and there can moreover be a perforation in the region of the kink, or there can be a notch together with a slit or use can be made of a notch together with a groove. Moreover, the kink can have both a perforation and a slit or a groove.

In a further aspect of the present invention, an insertion kit is proposed for inserting a biosensor into subcutaneous tissue of a user. This insertion kit comprises at least one biosensor in accordance with one or more of the above-described embodiments. Moreover, the insertion kit comprises at least one piercing element, for example at least one needle, at least one flat lancet, at least one round lancet, at least one cannula or combinations of the aforementioned and/or other piercing elements.

This insertion kit is intended to serve in providing the user with a simple way of independent insertion of the biosensor. To this end, the biosensor can enter into a direct functional neighborhood with the piercing element. Various options for arranging the biosensor with respect to the piercing element are conceivable.

By way of example, in one embodiment, the piercing element can be arranged between the two outer surfaces of the biosensor, for example between two pieces of the substrate which are separated from one another by the kink, for example between the above-described inner surfaces of the substrate pieces which can preferably be arranged parallel to one another.

By way of example, the piercing element can be introduced into the biosensor between the two outer surfaces and interact with the biosensor in such a way that the biosensor is introduced into the body of the user when a piercing aid or the piercing element pierces the body, and subsequently remains in the body of the user during the withdrawal of the piercing element. Furthermore, it is conceivable that the biosensor is arranged within e.g. a cannula and protected by the latter during the piercing process. It is also conceivable that one outer surface of the kinked biosensor is situated within the cannula while the second outer surface is arranged outside of the cannula during the piercing process.

A preferred embodiment is an insertion kit with a piercing element, more particularly a flat lancet, which is pushed through between the two outer surfaces and thereby comes into contact with the inner faces of the substrate. In the process, the piercing element, more particularly the flat lancet, can for example have a recess in order to hold a piece of the substrate situated between the two outer surfaces and thus render it possible in a simple fashion to carry along the biosensor during the piercing process. When the piercing element, more particularly the flat lancet, is withdrawn, the biosensor can preferably be left in the body of the user without further holding of the biosensor.

An alternative option for inserting the piercing element, more particularly the flat lancet, between the two outer surfaces lies in penetrating the substrate in the region of the kink such that the biosensor is held by the piercing element to the right and to the left of a tip of the piercing element, for example a lancet tip, while the tip protrudes freely from the substrate for piercing purposes, as will, for example, still be explained in more detail below in an exemplary fashion on the basis of FIG. 8.

By way of example, a flat lancet polished on one side is used as piercing element, which is deflected opposite to the polished side after entry into the tissue of the user. As a result, the angle between sensor and skin changes continuously, without the insertion angle being changed or reduced. The flat lancet can form an arc which makes better use of an anatomically available corridor of 2 to 10 mm under the skin surface.

An advantage of using a flat lancet over other piercing elements is that it displaces less tissue during the insertion and therefore potentially allows insertions which are less painful to the patient.

However, use can alternatively or additionally be made of a round lancet, around which the preferably flexible biosensor can be at least partly wound. Alternatively, use can also be made of a hollow needle and/or a cannula, within which the biosensor can be held, for example by virtue of the preferably flexible biosensor being held in rolled-together state. It is furthermore conceivable that the biosensor forms a polygon, which is inherently stable and can be introduced in this way into e.g. a hollow needle and/or a hollow cannula.

When a biosensor is inserted by means of the at least one piercing element, use can be made of very different geometries of biosensors, as already mentioned above. Thus, for example, electrodes and/or contacting elements can be situated on one outer surface only of the kinked biosensor, or these can be situated on both outer surfaces. Additionally, or alternatively, electrodes and/or contacting elements can likewise be situated on the inner side of the biosensor.

In general, the following embodiments are particularly preferred within the scope of the present invention:

Embodiment 1

A biosensor for insertion into subcutaneous tissue of a user, wherein the biosensor comprises at least one flexible substrate and at least one electrode on at least one surface of the substrate and at least one contacting element, wherein the contacting element is connected to the electrode, wherein the substrate has at least one kink, at which the substrate is at least partly kinked such that the surface is subdivided into at least two interconnected outer surfaces.

Embodiment 2

The biosensor according to the preceding embodiment, characterized in that at least one electrode is arranged in each case on at least two of the outer surfaces.

Embodiment 3

The biosensor according to one of the preceding embodiments, characterized in that the outer surfaces have at least two outer surfaces which are arranged substantially parallel to one another.

Embodiment 4

The biosensor according to one of the preceding embodiments, characterized in that the substrate is subdivided into at least two interconnected substrate pieces by the kink, wherein the substrate pieces are connected, more particularly adhesively bonded, to one another at least in part.

Embodiment 5

The biosensor according to one of the preceding embodiments, characterized in that the at least one electrode comprises at least one working electrode and/or at least one reference electrode and/or at least one counter electrode.

Embodiment 6

The biosensor according to one of the preceding embodiments, characterized in that at least one contacting element and/or at least one electrode are arranged on both the first and the second outer surface.

Embodiment 7

The biosensor according to one of the preceding embodiments, characterized in that the kink is arranged in the contacting element.

Embodiment 8

The biosensor according to one of the preceding embodiments, characterized in that at least one conductor track is arranged between the contacting element and the electrode.

Embodiment 9

The biosensor according to one of the preceding embodiments, characterized in that the substrate has an elongate structure and in that the one electrode and the contacting element are situated at mutually opposite ends of at least one of the outer surfaces.

Embodiment 10

A substrate blank for producing a biosensor according to one of the preceding embodiments, wherein the substrate blank has at least one flexible substrate and at least one electrode on at least one surface of the substrate and at least one contacting element, wherein the contacting element is connected to the electrode, wherein the substrate has at least one kink at which the substrate can be kinked at least in part such that the surface is subdivided into at least two interconnected outer surfaces.

Embodiment 11

The substrate blank according to the preceding embodiment, wherein the kink is formed in a fashion selected from the following: a slit, a perforation, a kink line with a groove or a combination therefrom.

Embodiment 12

An insertion kit for inserting a biosensor into subcutaneous tissue of a user, comprising at least one biosensor according to one of the preceding embodiments relating to a biosensor, furthermore comprising a piercing element.

Embodiment 13

The insertion kit according to the preceding embodiment, wherein the piercing element is selected from: a needle, a lancet, a flat lancet, a round lancet or a cannula.

Embodiment 14

The insertion kit according to one of the two preceding embodiments, wherein the piercing element is arranged between the two outer surfaces.

Embodiment 15

A method for producing a biosensor, more particularly a biosensor according to one of the preceding embodiments relating to a biosensor, comprising the following steps:
 providing at least one flexible substrate,
 applying at least one contacting element and at least one electrode connected to the contacting element to at least one surface of the substrate, kinking the substrate at at least one kink such that the surface is subdivided into at least two interconnected outer surfaces.

Embodiment 16

The method according to the preceding embodiment, wherein the biosensor has an elongate structure and the kinking takes place in a manner selected from: kinking parallel to an axis of longitudinal extent of the biosensor; kinking at an angle to an axis of longitudinal extent of the biosensor.

These and other features and advantages of the present invention will become more fully understood from the following detailed description of the invention taken together with the accompanying claims. It is noted that the scope of the claimed is defined by the recitations therein and not by the specific discussion of features and advantages set forth in the present description.

BRIEF DESCRIPTION OF THE SEVERAL VIEWS OF THE DRAWINGS

Further details and features of the invention emerge from the following description of preferred exemplary embodiments, in particular in conjunction with the dependent claims. Here, the respective features can be realized on their own or, some of them together, in a combination with one another. The invention is not restricted to the exemplary embodiments. The exemplary embodiments are illustrated schematically in the figures. Here, the same reference signs in the individual figures denote equivalent or functionally equivalent elements, or elements that correspond in terms of their function.

In detail:

FIG. 6a: shows an illustration of an unkinked biosensor with a kink in an electrode region;

FIG. 6b: shows an illustration of the biosensor from FIG. 6a with a kink in the electrode region;

Figure 1:
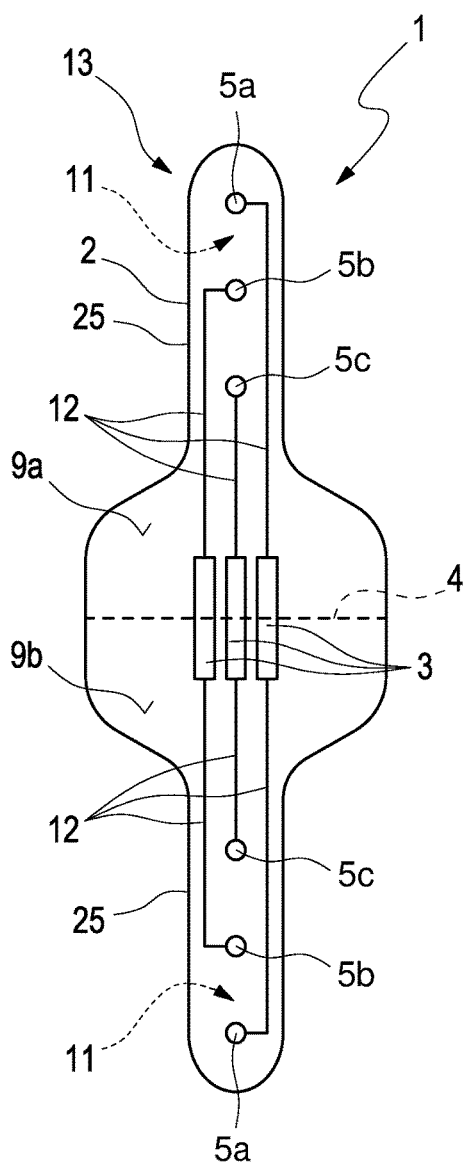
FIG. 1: shows a plan view of an unfolded biosensor with contacting elements and electrodes and a kink line.

Skilled artisans will appreciate that elements in the drawings are illustrated for simplicity and clarity and have not necessarily been drawn to scale. For example, the dimensions of some of the elements in the drawing figures may be exaggerated relative to the other elements to help improve the understanding of the embodiments of the present invention.

DETAILED DESCRIPTION OF THE INVENTION

For the purposes of describing and defining the present invention it is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

FIG. 1 schematically shows a biosensor 1 in an unkinked initial state, which simultaneously also constitutes an exemplary embodiment for a substrate blank 13. The biosensor 1 has a substrate 2, onto the one surface 9 of which contacting elements 3 have been applied, which are connected via conductor tracks 12 to electrodes 5, such as e.g. a working electrode 5a, a counter electrode 5b or a reference electrode 5c, on a first outer surface 9a of the substrate 2. The contacting elements 3 are in turn connected to further electrodes 5 via conductor tracks 12 on a second outer surface 9b of the substrate 2, wherein these further electrodes can in turn consist of an electrode set of working electrode 5a, counter electrode 5b and reference electrode 5c. It is likewise conceivable that contacting elements 3, which are not interconnected, are applied to the first outer surface 9a and to the second outer surface 9b. Further electrodes 5 and contacting elements 3 can also be applied to the biosensor 1; however, these are not shown here.

A kink 4 is applied in the region of the contacting elements 3, by means of which the biosensor 1 can be kinked after applying the contacting elements 3 or the electrodes 5 such that the substrate 2 is subdivided into two substrate pieces 25. If the biosensor 1 is kinked about the kink 4, the biosensor 10 has two interconnected outer surfaces (9a and 9b), which respectively have a region with contacting elements 3 and electrodes 5. Here, the contacting elements 3 on the two outer surfaces 9a, 9b are preferably situated at one end of the kinked biosensor 10. In this example in FIG. 1, the contacting elements 3 are furthermore respectively interconnected since the kink line 4 extends across the contacting elements 3 and is aligned through the latter. However, this is not mandatory. It is also possible that contacting elements 3 are attached only on one outer surface 9a, 9b 9c or that mutually separated contacting elements 3 are attached on a number of outer surfaces 9a, 9b, 9c. Likewise, after kinking the biosensor 1 about the kink 4, the electrodes 5 (specifically the working electrode 5a, the counter electrode 5b and the reference electrode 5c) lie on the first outer surface 9a, pointing in the same direction of the elongate shaft or of the elongate tongue 20 as the electrodes 5, 5a, 5b, 5c of the second outer surface 9b. It follows that, after kinking the biosensor 1 about the kink 4, the contacting elements 3 and the electrodes 5 of the electrode region 5d of the two outer surfaces 9a and 9b lie at opposite ends of the kinked biosensor 10. This renders it possible to ensure that contact elements 3 and electrodes 5 are not inserted simultaneously into the body of a user. The contacting elements 3 preferably remain outside of the body while the electrodes 5 come into contact with the bodily fluid of the user.

It is furthermore conceivable that, in addition to the electrodes 5 on the two outer surfaces 9a and 9b, electrodes 5 are also attached to the inner faces of the substrate 2. These inner faces, which are symbolically denoted by reference sign 11 in FIG. 1, are arranged on the rear side of the substrate 2 lying opposite to the surface 9 in the plan view in accordance with FIG. 1. In this embodiment (not shown here), the biosensor 1 is preferably kinked by less than 180° about the kink 4 such that the electrodes 5 on the inner face 11 are likewise accessible to the bodily fluid of the user in the inserted state. The electrodes 5 can likewise be connected via the contacting elements 3 on the outer surfaces 9a and 9b, or via further contacting elements 3 on the inner faces 11 or on one of the outer surfaces 9a or 9b.

Figure 2A:
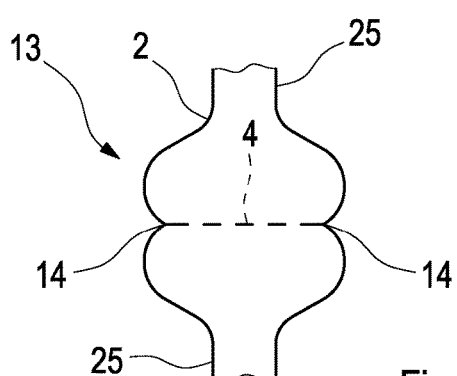
FIG. 2a: shows a plan view of a piece of a biosensor with a kink line, which provides a notch.
Figure 2B:
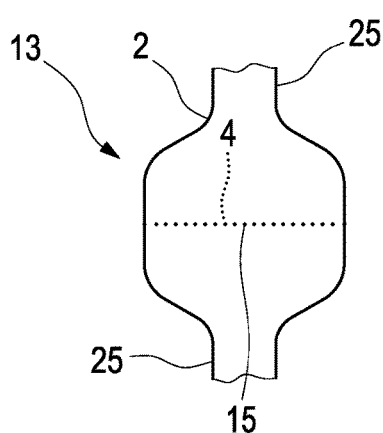
FIG. 2b: shows a plan view of an unkinked biosensor in the region of a kink with a perforation in a kink.

The kink 4 can be introduced into the biosensor 1 in various ways. Firstly, the substrate 2 itself can be manufactured from a very thin kinkable material such that the biosensor 1 can very easily be kinked at the kink 4. Secondly, the biosensor 1 can, as shown in FIG. 2a, have at least one notch 14 in the substrate 2 such that easy kinking becomes achievable in this region of the biosensor 1. As an alternative to the notch 14 from FIG. 2a, or in addition thereto, at least one perforation 15 in the substrate 2 can be used at the kink 4, as shown in FIG. 2b. By way of example, such a perforation 15 can have punctiform material ablations of the substrate 2 in the kink 4. As a result of these material voids, the substrate 2 or the biosensor 1 is weaker at this point and hence easier to kink.

Figure 2C:
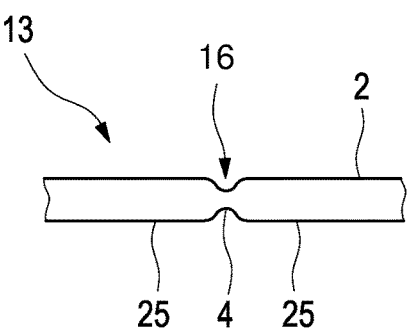
FIG. 2c: shows a side view of an unkinked biosensor with a kink with a groove on both sides.
Figure 3:
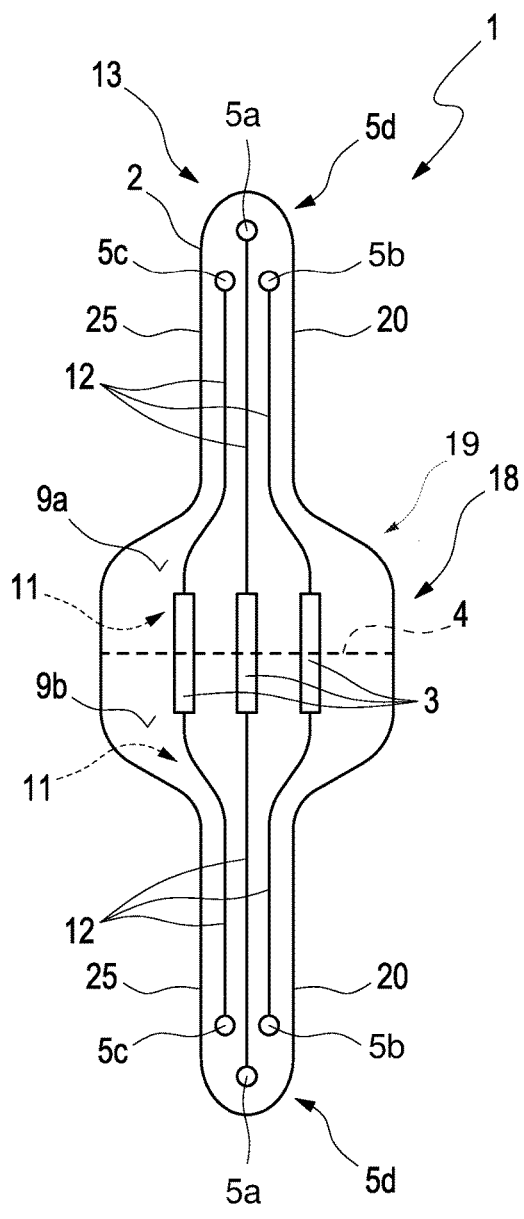
FIG. 3a: shows a plan view of a biosensor with a kink in the region of contacting elements.
FIG. 3b: shows an illustration of the biosensor in accordance with FIG. 3a after kinking.
Figure 3:
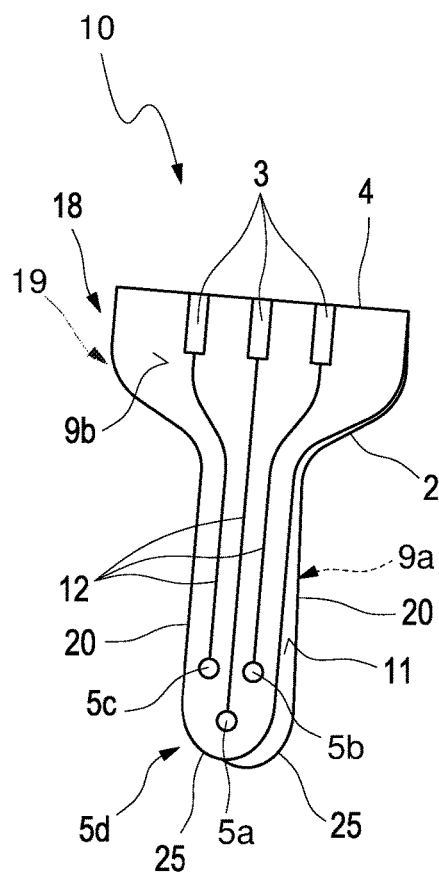
Figure 4:
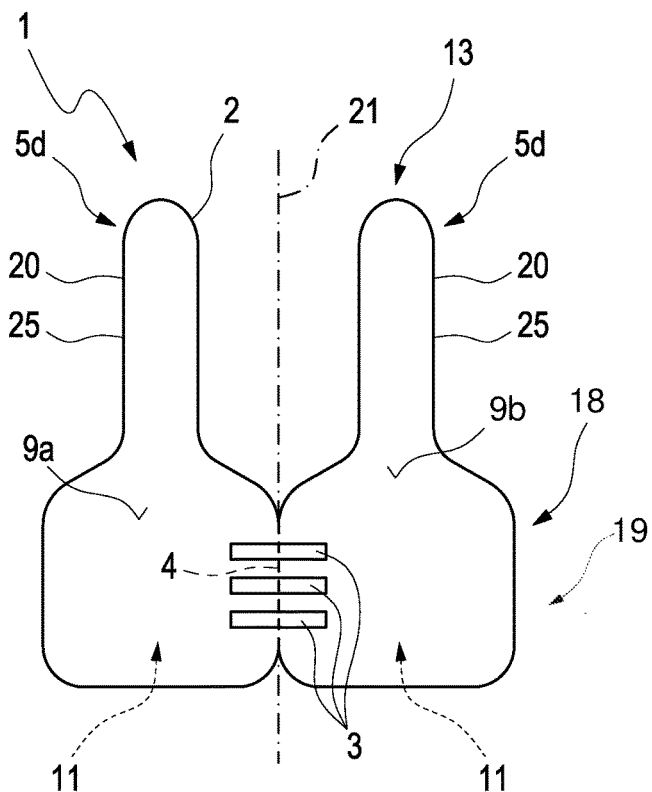
FIG. 4a: shows a plan view of a biosensor with a lateral kink.
FIG. 4b: shows an illustration of the biosensor from FIG. 4a after kinking.
Figure 4:
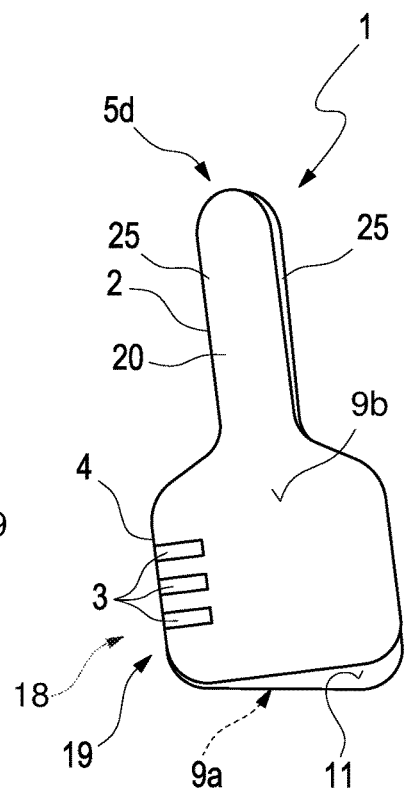
Figure 5:
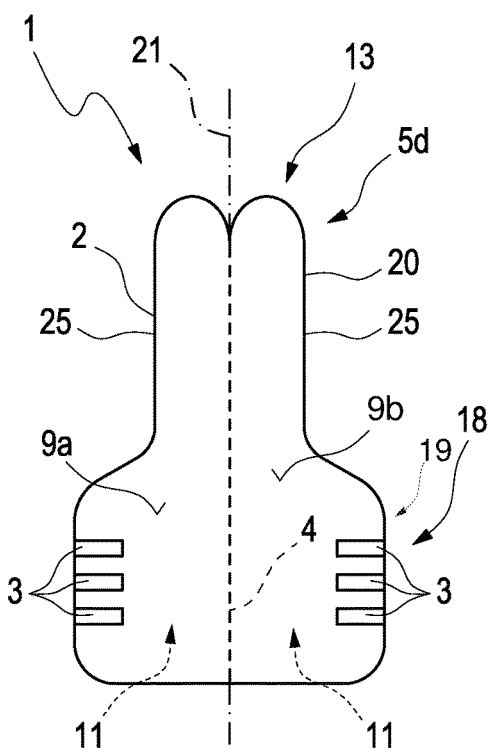
FIG. 5a: shows an illustration of an unkinked biosensor with a kink along the longitudinal side.
FIG. 5b: shows an illustration of the biosensor from FIG. 5a after kinking.
Figure 5:
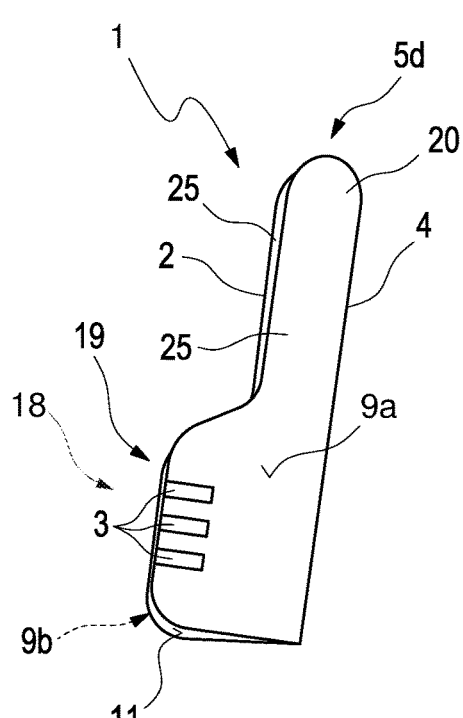

A further option for generating a kink 4 of the biosensor 1 which is more easily kinkable than the remaining substrate 2 of the biosensor 1 consists of producing the biosensor 1 from a thinner material or with less material at the kink 4 than in the remainder of the substrate 2, as shown in a side view of the substrate 2 in FIG. 2c. This type of material reduction in the kink region 4 of the biosensor 1 can be brought about on the basis of adaptations in the production process, as illustrated in FIG. 2c, by virtue of providing less material at the kink 4. By way of example, this is how a groove 16 or a slit can be created, wherein a groove 16 can, for example, comprise any one-sided or two-sided thinning of the material of the substrate 2, with, in principle, an arbitrary cross section, for example with a triangular or circular cross section, for example in the form of a flute and/or slot.

In the variant from FIG. 2a, the notch 14 will, for example, be introduced at the kink 4 before and/or during and/or after the production process of the biosensor 1, for example by stamping, cutting or by means of a chemical process, e.g. by etching. This can be undertaken on both sides of the substrate 2, as illustrated in FIG. 2a, or else on only one side of the substrate 2.

FIGS. 3a to 6b describe four preferred variants which, in principle, can also be combined and which substantially differ from one another in terms of at what points the kink 4 can be arranged on the biosensor 1 in order to generate a kinked biosensor 1 with two interconnected outer surfaces 9a, 9b after kinking at the kink 4.

FIG. 3a illustrates a biosensor 1 like in FIG. 1, which, as a main body, has a substrate 2, wherein the substrate 2 has an elongate form and has two tapered ends coming together in an approximately pointed or rounded-off fashion. Shown in the center of the biosensor 1 is a bulging section with a widening 18, which has the kink 4 in this case. The surface 9 is subdivided by the kink 4 into the two outer surfaces 9a and 9b, wherein the two outer surfaces 9a and 9b constitute the surfaces on which at least one contacting element 3 and one electrode 5 are applied, wherein the two outer surfaces 9a and 9b point outward after kinking about the kink 4 of the biosensor 1, as illustrated in FIG. 3b. The kinked biosensor 1 is symbolically denoted by reference sign 10.

In the specific case of the biosensor 1 from FIG. 3a, there are, for example, three contacting elements 3 on the surface 9 of the unkinked biosensor 1. The kink 4 extends through the contacting elements 3 such that, after the kinking process, a part of the contacting elements 3 is present on both the first outer surface 9a and on the second outer surface 9b, as shown in FIG. 3b. Each of these contacting elements 3 is, both on the first outer surface 9a and on the second outer surface 9b, connected to respectively one electrode 5 via conductor tracks 12 such that three electrodes 5, namely a working electrode 5a, a counter electrode 5b and a reference electrode 5c, are present on both the one pointed end of the biosensor 1 from FIG. 3a and on the second outer surface 9b, as illustrated schematically in FIG. 3b.

As can be identified from FIG. 3b, the kinked biosensor 10 has, at one end, a region with the contacting elements 3. This region is slightly widened compared to the shaft or the tongue 20, along which the conductor tracks 12 extend until they end at the pointed end of the kinked biosensor 10 in the electrodes 5, 5a, 5b, 5c. This subdivision of contacting elements 3 and electrodes 5 is particularly preferred because, for the use of the biosensor 10, only the electrode region 5d with the electrodes 5 should be introduced into the body of the patient together with part of the conductor track 12 in order to ensure contacting of the electrodes 5 with bodily fluid. The opposite contacting region 19 with the contacting elements 3 is preferably not introduced into the body, but provides the option for contacting the biosensor 10 with an electronic measuring instrument. Since the contacting elements 3 are produced slightly wider than the conductor tracks 12 and electrodes 5, the substrate 2 of the biosensor 1, 10 is designed slightly wider at this contacting region 19, as explained above, and equipped with the widening 18 in order to be able to undertake contacting which is as simple as possible with a measuring instrument. This widening 18 of the biosensor 1, 10, which, in principle, can be used in this or else in other exemplary embodiments, is also advantageous because this widening 18 prevents the sensor 10 as a whole from being able to penetrate the body of the patient.

FIGS. 4a and 4b in turn illustrate a biosensor 1 prior to the kinking process (FIG. 4a), and the same biosensor 1, 10 after the kinking process (FIG. 4b). Here too, the biosensor 1, 10 has a narrower tongue 20, which preferably holds the electrodes 5 and, optionally, conductor tracks 12 (not illustrated in FIGS. 4a and 4b; the arrangement is for example in accordance with FIGS. 3a and 3b), and a widening 18, which is provided with the contacting elements 3. In contrast to the biosensor 1 from FIG. 3a, the kink line 4 is not situated across an axis of longitudinal extent 21 of the biosensor 1, but is along this axis of longitudinal extent 21. In contrast to the example illustrated in FIG. 4a, the biosensor 1 can, in this or else in other exemplary embodiments, also have contacting elements 3 on only one of the two outer surfaces 9a and 9b such that, after the kinking process, contacting elements 3 are present on only one of the two outer surfaces 9a or 9b. As a result of arranging the kink line or kink 4 parallel to the tongues 20 of the biosensor 1, the biosensor 10, after the kinking process, does not stick together with its outer surfaces 9a and 9b at an upper or lower edge of the biosensor 10, but rather on a lateral edge of the two surfaces 9a and 9b. Here, the two sides of the substrate 2 lying opposite the two outer surfaces 9a and 9b form the inner faces 11 of the substrate 2 after the kinking process, as also shown in FIGS. 3b, 4b and 6b.

An alternative geometric embodiment of the biosensor 1 is shown in FIGS. 5a and 5b, in which the biosensor 1 prior to the kinking process only has an elongate extent in one direction. Here, a tongue 20 extends in an elongate fashion in a direction of an axis of longitudinal extent 21, wherein, at an end region of the tongue 20, electrodes 5 can be arranged, as well as, optionally, one or more conductor tracks 12, which are not illustrated in FIGS. 5a and 5b. Furthermore, the biosensor 1 once again has a widening 18, which holds contacting elements 3. In this exemplary embodiment, a kink 4, which, for example, can once again be embodied as kink line, extends preferably symmetrically through the regions of the widening 18 with the contacting elements 3 and the narrower tongue 20 with an electrode region 5d of the biosensor 1, 10. For the kinking process, the kink 4 preferably lies in the tongue 20, which extends in an elongate fashion, preferably runs together in a pointed or rounded-off manner, and extends through the latter up to the opposite widening 18, in which the contacting elements 3 are present.

During the kinking process of the biosensor 1 from FIG. 5a, the sensor 1 is kinked along the kink line 4, such that, for example, the tongue 20 with the electrodes 5 can be arranged on the one side. Furthermore, the kinking process can take place in such a way that a contacting region 19 only extends in one direction, with the contacting elements 3. In the biosensors 10 from FIGS. 4b and 5b, there is preferably a lateral contacting of the biosensor 10, which can lead to different geometries of a measurement arrangement within a sensor system.

In a further example of a biosensor 1, illustrated in FIG. 6a, only electrodes 5 are indicated schematically in the center of an elongate tongue 20, wherein the elongate tongue 20, at its mutual opposing ends, respectively opens into a widening 18 to the right and left of an axis of longitudinal extent 21. Contacting elements 3 can preferably be arranged in one or both of these widenings 18. If the second outer surface 9b is now folded backwards along a kink 4 of the biosensor 1, aligned perpendicular to the axis of longitudinal extent 21 in an exemplary fashion in this exemplary embodiment, then the biosensor 1 reaches its final position in the form of the kinked biosensor 10, as shown in FIG. 6b. Here, as also already shown in the variants from FIGS. 3b, 4b and 5b, the kinked biosensor 10 has a pointed or rounded off running together electrode region 5d, which is connected to the contacting elements 3 by the elongate tongue 20 with the widening 18 and the contacting region 19. In the specific case of the kink line arrangement from FIG. 6a, the two tongues 20 of the kinked biosensor 10 from FIG. 6b are interconnected in the electrode region 5d between its outer surfaces 9a and 9b.

In all these embodiments from FIGS. 1 to 6b, contacting elements 3 and electrodes 5 as well as the conductor tracks 12 between the contacting elements 3 and electrodes 5 can be provided on both outer surfaces 9a and 9b or else on only one of the two outer surfaces 9a or 9b.

Figure 7:
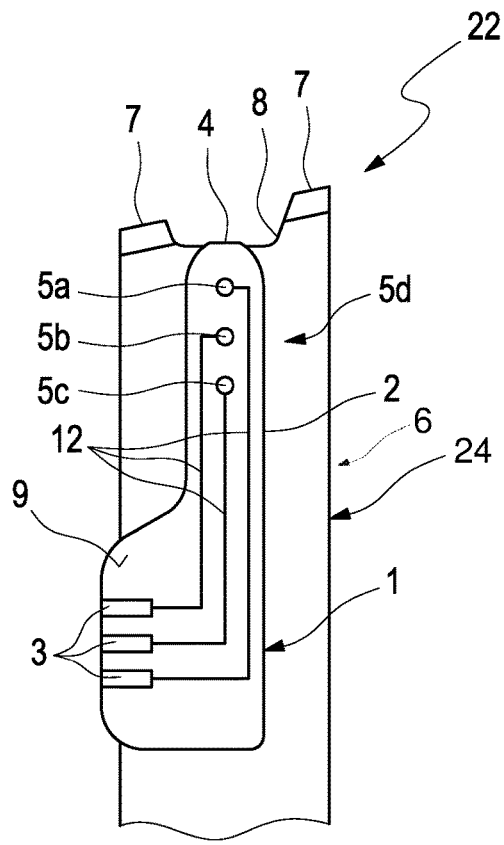
FIG. 7: shows an illustration of a kinked biosensor in the electrode region with an inserted lancet.

In order to introduce such a biosensor 1, 10 from FIG. 3b, 4b, 5b or 6b into the body of a patient, it is possible, as shown in FIG. 7, for example to use an insertion kit 22, which comprises at least one piercing element 24 in addition to the at least one biosensor 1, 10. This piercing element 24 is illustrated in an exemplary fashion in FIGS. 7 and 8 in the form of a lancet 6. In particular, the piercing element 24 can be pushed between the two outer surfaces 9a and 9b or inner faces 11 of the kinked biosensor 10 such that, for example, the piercing element 24 comes into contact with the inner faces 11 of the substrate 2.

FIG. 7 shows a lancet 6 with an elongate polished section on one lancet tip 7, wherein this polished section has a recess 8 in the lancet tip 7 in order to be able to hold the kinked biosensor 10 at its kink 4. This recess 8 preferably does not have a polished section so as not to damage the sensor 10. Since the two outer surfaces 9a and 9b are interconnected at the kink 4 in the biosensor 10, the biosensor 1, 10 can be introduced into the body of the patient without any further aids by piercing the lancet 6 into said body, and the biosensor remains in the body of the patient after withdrawing the lancet 6, preferably without further utensils.

Figure 8:
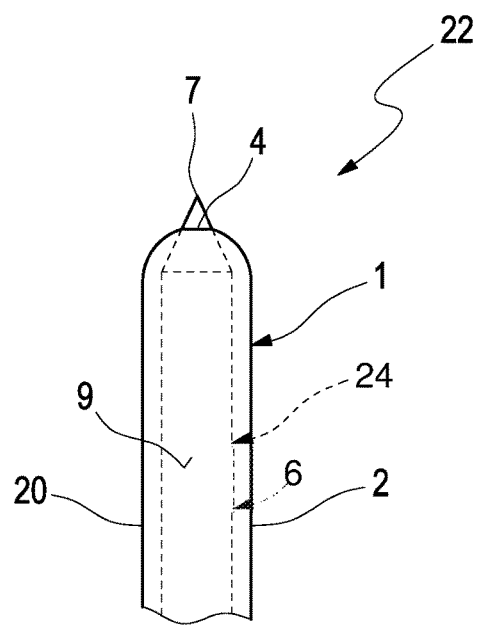
FIG. 8: shows an illustration of a kinked biosensor with inserted lancet, wherein the lancet tip is guided through the kink.

An alternative embodiment of the insertion kit 22 with an alternative arrangement of a lancet 6 and of a kinked biosensor 10 is shown in FIG. 8. Here, the lancet 6 extends within the kinked biosensor 10, for example within a tongue 20 of the kinked biosensor 10. The lancet 6 can, in particular, once again extend between the two outer surfaces 9a and 9b, in contact with the inner faces 11 of the substrate 2 of the biosensor 10. The lancet 6 from FIG. 8 for example has lancet tip 7, which comes together at a point and which is pierced through the substrate 2 of the biosensor 10 at the kink 4 such that the biosensor 10 can likewise be introduced into the body of the user together with the lancet 6.

Further options are conceivable as an alternative to the two options shown in FIGS. 7 and 8 for inserting the biosensor 1, 10 into the body of the user. In particular, the piercing element 24 of an insertion kit 22 can be embodied in a different fashion. By way of example, provision can be made for a hollow cannula, into which the tongue 20 of the biosensor 1, 10 and/or another piece of the biosensor 1, 10 is introduced in such a fashion that these are protected during the piercing process.

Figure 9:
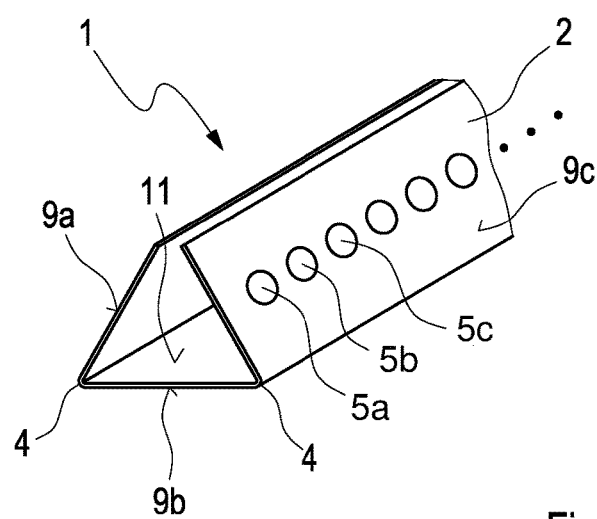
FIG. 9: shows an illustration of a biosensor with a number of kinks.

A further embodiment of the biosensor 10 after one or more kinking processes is illustrated in FIG. 9. Here, a biosensor 10 with two kink lines 4 is illustrated schematically, which biosensor has three outer surfaces 9a, 9b, 9c. As a result of the angled arrangement of the three outer surfaces 9a, 9b, 9c with respect to one another, the biosensor 10 in FIG. 9 has a three-dimensional design with a polygonal cross section, in this case, in an exemplary fashion, a triangular cross section. In FIG. 9, a plurality of electrodes 5 are shown in an exemplary fashion on a third outer surface 9c. The electrodes denoted here by reference sign 5 can optionally be or comprise one or more working electrodes 5a, one or more counter electrodes 5b and/or one or more reference electrodes 5c. However, another embodiment of the electrodes 5 is also possible, for example an embodiment deviating from the embodiment in FIG. 9 in respect of the number, the use, or the arrangement of the electrodes 5. By way of example, as already described above, but not illustrated here, the electrodes 5 are connected to at least one contacting element 3 on the biosensor 10 by means of one or more conductor tracks 12.

Further functional elements, such as working and/or counter and/or reference electrodes and/or contacting elements 3 as well as conductor tracks 12, can be situated on one or two further ones of the three outer surfaces 9a, 9b, 9c. Furthermore, one or more functional elements such as working electrodes 5a, counter electrodes 5b, reference electrodes 5c or contacting elements 3, can, in addition or as an alternative thereto, be situated on the inner faces 11 of the biosensor 10, but this is not shown here.

As already described above, further three-dimensional embodiments of the biosensor 1 as a result of multiple kinking at multiple kinks 4 are conceivable. Thus, there is no need for the kinks 4 all to extend parallel to one another, as shown in this example, but rather they can also extend obliquely or across one another and can also cross in the process. By way of example, regions with functional elements on a first outer surface 9a can be separated from regions without functional elements on a second outer surface 9b by one or more kinking processes. Moreover, a kinking process can serve to kink the biosensor 10 about a lancet 6, for example a needle, for example in order to affix said biosensor to the needle for an insertion.

Having described the invention in detail and by reference to specific embodiments thereof, it will be apparent that modifications and variations are possible without departing from the scope of the invention define in the appended claims. More specifically, although some aspects of the present invention are identified herein as preferred or particularly advantageous, it is contemplated that the present invention is not necessarily limited to these preferred aspects of the invention.

LIST OF REFERENCE SIGNS

1 Biosensor
2 Substrate
3 Contacting element
4 Kink
5 Electrode
5a Working electrode
5b Counter electrode
5c Reference electrode
5d Electrode region
6 Lancet
7 Lancet tip
8 Recess in lancet tip
9 Surface of the substrate
9a First outer surface of the substrate
9b Second outer surface of the substrate
9c Third outer surface of the substrate
10 Kinked biosensor
11 Inner face of the substrate
12 Conductor track
13 Substrate blank
14 Notch
15 Perforation
16 Groove or slit
18 Widening
19 Contacting region
20 Tongue, shaft
21 Axis of longitudinal extent
22 Insertion kit
24 Piercing element
25 Substrate piece

The invention claimed is:

1. A biosensor configured for insertion into subcutaneous tissue of a user for one or more of qualitative or quantitative detection of at least one analyte in a bodily fluid, the biosensor comprising:
a flexible substrate having an electrical pattern on a surface of the substrate;
the substrate having a kink at which the substrate is at least partly kinked, the kink dividing the surface into two interconnected outer surfaces and dividing the substrate into two substrate halves and two electrical pattern halves, wherein each electrical pattern half has at least one electrode portion, the electrode portion being one or both of a portion of a working electrode and a portion of a further electrode, and wherein each electrical pattern half further has at least one portion of a contacting element connected to the respective electrode portion, and wherein the substrate halves and the electrical pattern halves have substantially the same shape, and wherein the electrical pattern is disposed on the two outer surfaces of the biosensor when the biosensor is folded about the kink and inserted into the subcutaneous tissue of a user.

2. The biosensor of claim 1 wherein the electrode portion comprises a plurality of electrodes and at least one of the electrodes is arranged on each of the two outer surfaces.

3. The biosensor of claim 1 wherein the two outer surfaces are arranged substantially parallel to one another.

4. The biosensor of claim 1 wherein the substrate halves are connected to one another at least in part.

5. The biosensor of claim 4 wherein the substrate halves are adhesively bonded to one another at least in part.

6. The biosensor of claim 1 wherein the electrode portion comprises one or more of at least one working electrode, at least one reference electrode or at least one counter electrode.

7. The biosensor of claim 1 wherein one or more of the contacting element or the electrode portion are arranged on both the first and the second outer surface.

8. The biosensor of claim 1 wherein the kink is arranged in the contacting element.

9. The biosensor of claim 1 wherein a conductor track is arranged between the contacting element and the respective electrode portion.

10. The biosensor of claim 1 wherein the substrate has an elongate structure and the electrode portion and the contacting element are situated at mutually opposite ends of one of the outer surfaces.

11. The biosensor of claim 1, wherein the substrate is symmetrical about an axis defined by the kink, whereby the two electrical pattern halves overlie one another when the substrate is folded about the kink.

12. The biosensor of claim 1, wherein the contacting element is folded at the kink.

13. The biosensor of claim 1, wherein the two substrate halves are adhered to one another.

* * * * *